United States Patent [19]

Hallgren et al.

[11] 4,234,504

[45] Nov. 18, 1980

[54] CARBONYLATION PROCESS

[75] Inventors: John E. Hallgren, Scotia; William E. Smith, Schenectady, both of N.Y.

[73] Assignee: General Electric Company, Schenectady, N.Y.

[21] Appl. No.: 969,681

[22] Filed: Dec. 15, 1978

[51] Int. Cl.$^3$ ............................................. C07C 68/00
[52] U.S. Cl. ................................................... 260/463
[58] Field of Search ........................................ 260/463

[56] References Cited

U.S. PATENT DOCUMENTS

| | | | |
|---|---|---|---|
| Re. 29,338 | 8/1977 | Perrotti et al. | 260/463 |
| 3,226,418 | 12/1965 | Anderson et al. | 260/463 |
| 3,227,740 | 1/1966 | Fenton | 260/463 |
| 3,359,296 | 12/1967 | Newallis et al. | 260/463 |
| 3,952,045 | 4/1976 | Gaenzler et al. | 260/463 |
| 4,113,762 | 9/1978 | Gaenzler et al. | 260/463 |

FOREIGN PATENT DOCUMENTS 45-24966 8/1970 Japan ........................................ 260/463

*Primary Examiner*—Donald G. Daus
*Assistant Examiner*—M. C. Eakin
*Attorney, Agent, or Firm*—F. Wesley Turner; James C. Davis, Jr.; Joseph T. Cohen

[57] ABSTRACT

A carbonylation process which comprises contacting a β-fluoroalkanol, carbon monoxide, a base, and the Group IIB element mercury present in an oxidation state greater than zero. The resulting β-fluoroaliphatic carbonates can be employed in combination with alkanols and/or phenols to prepare aliphatic and aromatic mono- and polycarbonates. The resulting carbonates are useful in a wide variety of applications, especially polycarbonates which can be molded or formed into films, sheets, fibers, laminates, or reinforced plastics by conventional techniques.

33 Claims, No Drawings

CARBONYLATION PROCESS

CROSS REFERENCE TO RELATED APPLICATIONS

This invention is related to copending U.S. patent application Ser. Nos. 969,682 of J. E. Hallgren and W. E. Smith, and 969,683 and 970,058 of D. J. Brunelle and W. E. Smith, filed on Dec. 15, 1978. The aforesaid applications are assigned to the same assignee as the assignee of this application and all the disclosures contained therein are hereby incorporated herein in their entirety by reference.

BACKGROUND OF THE INVENTION

1. Field of the Invention

This invention relates to a carbonylation process which comprises contacting a $\beta$-fluoroalkanol, carbon monoxide a base, and the Group IIB element mercury having an oxidation state greater than zero. The resulting $\beta$-fluoroaliphatic carbonates can be employed in situ or isolated from the reaction mixture in the preparation of mono- or polycarbonates.

2. Description of the Prior Art

The synthesis of bis(2,2,2-trifluoroethyl)carbonate by the reaction of $\beta$-trifluoroethanol with phosgene is described by Aldrich & Shepard (J. Org. Chem. 29, 11 (1964).

DESCRIPTION OF THE INVENTION

This invention embodies a carbonylation process comprising contacting a $\beta$-fluoroalkanol, carbon monoxide, a base, and the Group IIB element mercury having an oxidation state greater than zero to form a $\beta$-fluoroaliphatic carbonate.

The reactants and the resulting reaction products of the process can be illustrated by the following equations which are furnished for illustrative purposes only since the reactants, reaction products, reaction mechanisms, etc. involved in the preparation of $\beta$-fluoroaliphatic carbonates can be different and/or more complex:

$$2CF_3CH_2OH + Hg(OCOCH_3)_2 + CO \longrightarrow \qquad (I)$$
$$(CF_3CH_2O)_2CO + Hg° + CH_3COOH,$$

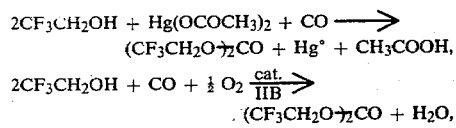

$$(II)$$

$$(CF_3CH_2O)_2CO + H_2O,$$

Any $\beta$-fluoroalkanol can be used in our process and is defined herein in the appended claims as a "$\beta$-fluoroalkanol". Illustratively, the $\beta$-fluoroalkanol reactant can be described by the generic formula:

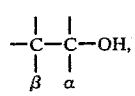

(III)

which describes the essential features of a $\beta$-fluoroalkanol reactant, i.e. alkanols of the class wherein at least one hydroxyl group is separated from a fluorinated carbon atom by at least two carbon atoms. Further, illustratively with primary alkanols fluorine atoms are at least located on a single $\beta$ carbon, with secondary alkanols fluorine atoms are at least located on either or both $\beta$-carbon atoms, and with tertiary alkanols fluorine atoms are at least located on any of three $\beta$-carbon atoms. The fluorine atoms, as illustrated by the specific examples set out hereafter, can be associated with any $\beta$ carbon atom as well as other carbon atoms—subject to the above class requirement. In a presently preferred embodiment primary or secondary fluorinated alkanols, more preferably in that order, are employed since the reactivity of $\beta$-fluorinated primary alkanols is generally greater than $\beta$-fluorinated secondary alkanols, whose reactivity is generally greater than $\beta$-fluorinated tertiary alkanols. Further, the alkanols can be mono- or polyhydroxy-functional. Broadly, the $\beta$-fluoroalkanols can be carbo or heteromonocyclic, polycyclic or fused polycyclic and can have two or more cyclic systems (monocyclic, polycyclic or fused polycyclic systems) which are connected to each other by single or double valence bonds or multivalent radicals. Further, presently preferred are $\beta$-trifluoroalkanol reactants which contain from 2–10 carbon atoms, and more preferably from 2–4 carbon atoms. Illustrative of commercially important $\beta$-fluoroalkanols include the following:

$CH_2FCH_2OH$, $CHF_2CH_2OH$, $CF_3CH_2OH$, $(CF_3)_2CHOH$, $CF_3CF_2CH_2OH$,

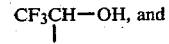

, etc.

The Group IIB element is defined herein and in the appended claims as "Group IIB element mercury". The Group IIB element mercury can be present in ionic, inorganic or organic compound or complex, etc., forms. The Group IIB element mercury can be employed in oxide, halide, nitrate, sulfate, oxalate, acetate, propionate, phosphate, thiocyanate, etc., form. Group IIB element mercury in complex form, e.g., with ligands, such as ammonia, amines, phosphines, etc., can also be employed. Presently preferred Group IIB mercury entities form homogeneous mixtures when combined with the reactants, especially when the process is carried out under liquid phase reaction conditions.

The Group IIB element mercury can be employed in any of its oxidation states including zero, as well as any oxidation state greater than zero including plus one, plus two, etc.

Illustratively, Group IIB elemental, compound or complex forms of mercury are commonly described as follows: $Hg$, $Hg_2CN_2$, $[Hg(NH_3)_2]Cl_2$, $[Hg(NH_3)_4]Br_2$, $[Hg(ClCH=CH)Cl]$, $[Hg(CH=CH)Cl]Cl$, $HgNH_2Cl$, $[(C_5H_3)_3P]_2Hg_2Br_4$, $[(C_6H_5)_3P]_2Hg_2Cl_2$, $Cu_2[HgI_4]$, $Co[Hg(SCN)_4]$, $K_2[Hg(CH_3C_6H_3S_2)_2]$, $HgCl_2$, $HgO$, etc.

To enhance the rate of reaction and to reduce the quantity of Group IIB mercury employed, an oxidant can be employed in our process subject to the proviso that the oxidant has an oxidation potential greater than or more positive than the Group IIB mercury element, compound, or complex employed as the catalytic species. Preferred oxidants comprise any element, compound or complex of "a periodic Group" IIIA, IVA, VA, VIA, VIIA, IB, IIB, IVB, VB, VIB, VIIB, VIIIB, lanthanides or actinide having an oxidation potential greater than or more positive than "the Group IIB element mercury". Typical well-known oxidants of the Group IIB element mercury are compounds or complexes of copper, iron, manganese, cobalt, mercury, lead, cerium, vanadium, uranium, bismuth, chromium, etc. Wherein the oxidant is employed in salt form, the anion portion of the salt may be a $C_{1-20}$ carboxylate, halide, nitrate, sulfate, etc., and preferably is a halide, e.g. chloride, bromide, iodide, or fluoride. Illustrative of typical oxidants are cupric chloride, cupric bromide, cupric nitrate, cupric sulfate, cupric acetate, etc. In addition to the compounds described above, elements commonly employed as oxidants in elemental form, e.g. oxygen, ozone, chlorine, bromine, fluorine, etc., may be employed as the sole oxidant in the herein claimed process. Frequently, compounds or complexes of a periodic Group IIIA, IVA, VA, VIA, VIIA, IB, IIB, IVB, VB, VIB, VIIB, VIIIB, lanthanide or actinide are preferably employed as a redox co-catalyst of a periodic Group VIA or VIIA element, e.g. oxygen, sulfur, selenium, fluorine, chlorine, bromine, iodine, etc., including mixtures thereof, in order to enhance the rate of oxidation of a Group IIB mercury element, compound, or complex.

Any periodic Group element, compound or complex redox co-catalyst can be employed and comprises any element, compound or complex which catalyzes the oxidation of "the Group IIB mercury element, compound or complex" in the presence of an oxidant from a lower oxidation state to a higher oxidation state. In a presently preferred embodiment, oxygen is employed as a sole oxidant in combination with a redox co-catalyst selected from "a periodic Group" element, compound or complex. Any source of oxygen can be employed, i.e. air, gaseous oxygen, liquid oxygen, etc. Preferably either air or gaseous oxygen is employed.

As used herein and in the appended claims, the expression "complexes" includes coordination or complex compounds well-known to those skilled in the art such as those described in *Mechanisms of Inorganic Reactions*, Fred Basolo and Ralph G. Pearson, 2nd Edition, John Wiley and Sons, Inc. (1968). These compounds are generally defined herein as containing a central ion or atom, i.e. "a periodic Group" IIIA, IVA, VA, VIA, VIIA, IB, IIB, IVB, VB, VIB, VIIB, VIIIB, lanthanide or actinide element and a cluster of atoms or molecules surrounding a periodic group element. The complexes may be nonionic, cationic or anionic, depending on the charges carried by the central atom and the coordinated groups. The coordinated groups are defined herein as ligands, and the total number of attachments to the central atom is defined herein as the coordination number. Other common names for these complexes include complex ions (if electrically charged), Werner complexes, coordination complexes or, simply, complexes.

The process can be carried out in the absence of any solvent, e.g. where the $\beta$-fluoroalkanol reactant acts as both solvent and reactant. Representative of solvent species, preferably aprotic, which can be employed are the following: N-methylformamide, N,N-dimethylformamide, acetonitrile, nitrobenzene, $\gamma$-butyrolactone, nitromethane, dimethylsulfoxide, sulpholane and N-methylpyrrolidone, etc., and mixtures thereof.

This process is carried out under basic reaction conditions. Representative of basic species which can be employed are the following: elemental alkali and alkaline earth metals, basic quaternary ammonium, quaternary phosphonium or tertiary sulfonium compounds; alkali or alkaline earth metal hydroxides; salts of strong bases and weak organic acids; primary, secondary, or tertiary amines; etc. Specific examples of the aforementioned are sodium, potassium, magnesium metals, etc.; quaternary ammonium hydroxide, tetraethyl phosphonium hydroxide, etc.; sodium, potassium, lithium, and calcium hydroxide; quaternary phosphonium, tertiary sulfonium, sodium, lithium and barium carbonate; sodium acetate; sodium benzoate; sodium methylate; sodium thiosulfate; sodium compounds, e.g. sulfide, tetrasulfide, cyanide, hydride and borohydride; potassium fluoride; methylamine; isopropylamine; methylethylamine; allylethylamine; ditertbutylamine, dicyclohexylamine; dibenzylamine; tertbutylamine; allyldiethylamine; benzyldimethylamine; diacetylchlorobenzylamine; dimethylphenethylamine; 1-dimethylamino-2-phenylpropane; propanediamine; ethylenediamine; N-methylethylenediamine; N,N'-dimethylethylenediamine; N,N,N'-tritertbutylpropanediamine; N,N',N',N"-tetramethyldiethylenetriamine; pyridine; aminomethylpyridines; pyrrole; pyrrolidine; piperidine; 1,2,2,6,6-pentamethylpiperidine; imidazole; etc. Especially preferred bases are the hydroxides of lithium, sodium, potassium, calcium or barium; sodium, lithium or barium carbonate; sodium acetate; sodium benzoate, sodium methylate, lithium, sodium or potassium salts of 2,2,2-trifluoroethanol, etc., including mixtures thereof.

Although not required and accordingly—optionally, the process can be carried out in the presence of an organic phase transfer agent (PTA) including any onium phase transfer agent, e.g. quaternary ammonium hydroxide, tetraethyl phosphonium hydroxide, etc., as described by C. M. Starks, J.A.C.A. 93, 195 (1971); any crown ether phase transfer agent, e.g. Aldrichimica ACTA 9, Issue #1 (1976) Crown Ether Chemistry:Principles and Applications, G. W. Gokel and H. D. Durst, as well as C. J. Pederson in U.S. Pat. No. 3,622,577, etc.; any chelated cationic salt, e.g. alkaline or alkali earth metal diamine halides; cryptates, etc., i.e. any agent which is soluble in the organic phase and which enhances the transfer, maintenance, or retention of a cation, e.g. a halide.

Any amount of $\beta$-fluoroalkanol, the Group IIB mercury element compound or complex, oxidant including redox cocatalyst, base, ligand associated with the Group IIB element mercury, solvent, phase transfer agent, drying agent, carbon monoxide, etc., can be employed.

Illustratively, on a mole ratio basis relative to the $\beta$-fluoroalkanol, unless otherwise stated, the following reaction parameters can be employed:

Any amount of Group IIB element mercury can be employed. For example, Group IIB element mercury to $\beta$-fluoroalkanol mole proportions within the range of from about 0.001:1 or lower to about 1000:1 or higher are effective, however, preferably ratios of from 0.1:1 to 10:1, and more preferably at least 1:1 are employed in order to insure that optimum conversion of $\beta$-fluoroalkanol to $\beta$-fluoroaliphatic carbonate occurs.

Any amount of base can be employed. Generally effective mole ratios of base to the Group IIB element mercury are within the range of from about 0.000001:1 to about 100:1 or higher, preferably from 0.5:1 to about 10:1, and more preferably from 1:1 to 2:1.

Any amount of the oxidant can be employed. For example, oxidant to β-fluoroalkanol mole proportions within the range of from about 0.001:1 or lower to about 1000:1 or higher are effective; however, preferably ratios from 0.1:1 to 10:1 are employed to insure an optimum conversion of β-fluoroalkanol to β-fluoroaliphatic carbonate.

Any amount of redox co-catalyst component can be employed. For example, redox co-catalyst to β-fluoroalkanol mole proportions within the range of from about 0.0001:1 or lower to about 1000:1 or higher are effective; however, preferably ratios of from 0.0001:1 to 1:1, and more preferably 0.001:1 to 0.01:1 are employed.

As stated before, although not required, a phase transfer agent can be employed. Any amount can be employed. Generally effective mole ratios of phase transfer agent to the Group IIB element mercury are within the range of from about 0.00001:1 to about 1000:1 or higher, preferably from about 0.05:1 to about 100:1 and more preferably from about 10:1 to 20:1.

Although not required—as stated before, a solvent, preferably inert, can be employed. Any amount can be employed. Generally optimum solvent to β-fluoroalkanol reactant mole proportions are from 0.5:99.5 to 99.5:0.5, preferably from 50:50 to 99:1.

Any amount of carbon monoxide can be employed. Preferably the process is carried out under positive carbon monoxide pressure, i.e., where carbon monoxide is present in at least amounts sufficient to form the desired β-fluoroaliphatic carbonate. In general, carbon monoxide pressures within the range of from about ½ to about 500 atmospheres, or even higher, can be employed with good results. Presently preferred are CO pressures within the range of from 1 to 200 atmospheres.

Any reaction time period can be employed. Generally optimum reaction time periods are about 0.1 hour or even less to about 10 hours or even more.

Any reaction temperature can be employed. In general, optimum reaction temperatures are 0° C. or even lower to 200° C. or even higher and more often 0° C. to 50° C.

Although the foregoing generally describes reactions involving β-fluoroalkanols to form fluorinated aliphatic carbonates, this invention also includes a carbonylation process wherein β-fluoroalkanols plus other alcohols and/or phenols react in accordance with the process parameters described herein to form β-fluoroaliphatic mixed carbonates. Accordingly, the scope of the reaction products of this invention include compounds of the generic formula:

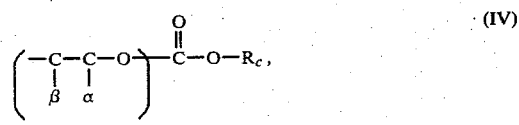

(IV)

wherein β-fluoroaliphatic carbonate is formed having at least two oxy groups both of which are independently and directly bonded to the same carbonyl carbon atom subject to the proviso that at least one of the oxy groups is separated from any β-fluorine atoms by at least two β-aliphatic carbon atoms, R$_c$ being a

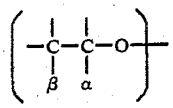

group, or an alkyl, a cycloalkyl, or aryl radical, including combinations thereof.

In order that those skilled in the art may better understand my invention, the following examples are given which are illustrative of the best mode of this invention, however, these examples are not intended to limit the invention in any manner whatsoever. Unless otherwise specified, all parts are by weight and all reaction products were verified by gas chromatography-mass spectrometry (gc-ms).

EXAMPLE I

A 50 ml. three-neck flask equipped with a subsurface CO inlet was charged with 25 ml. of CF$_3$CH$_2$OH—2,2,2-trifluoroethanol, 3.18 g. (10.0 mmol.) of Hg(II)(OAc)$_2$—mercury(II) diacetate, and 2.0 g. (13 mmol.) of 1,2,2,6,6-pentamethylpiperidine (PMP). CO was bubbled through the mixture for 16 hr. An additional 2.0 g. of PMP was added and CO addition was continued for 8 more hours. 15 ml. of a 1.0 molar solution of the sodium salt of dimethyl sulfoxide in dimethyl sulfoxide was added. The mixture was stirred for 3 more hours. Gas phase chromotography (gpc) showed the presence of 2.03 g. (90% yield) of bis(2,2,2-trifluoroethyl) carbonate of the formula (CF$_3$CH$_2$O)$_2$CO.

Although the above example has illustrated various modifications and changes that can be made in carrying out my process, it will be apparent to those skilled in the art that other changes and modifications can be made in the particular embodiments of the invention described which are within the full intended scope of the invention as defined by the appended claims.

We claim:

1. A carbonylation process which comprises contacting a β-fluoroalkanol, carbon monoxide, a base, and the Group IIB element mercury present in an oxidation state greater than zero, and subsequently recovering at least a portion of a resulting β-fluoroaliphatic carbonate.

2. The claim 1 process, further comprising a solvent.

3. The claim 2 process, further comprising an aprotic solvent.

4. The claim 1, 2 or 3 process, wherein said element is present in an ionic form.

5. The claim 1, 2 or 3 process, wherein said element oxidation state is at least +1.

6. The claim 2 or 3 process, wherein said base is a sterically hindered amine.

7. The claim 1, 2 or 3 process, wherein said element oxidation state is at least +2.

8. The claim 1, 2 or 3 process, wherein said element is associated with a halide.

9. The claim 1, 2 or 3 process, wherein said element is coordinated with a ligand.

10. The claim 1, 2 or 3 process, wherein said element is associated with an inorganic halide compound.

11. A carbonylation process which comprises contacting a β-fluoroalkanol, carbon monoxide, a base, the Group IIB element mercury, and an oxidant having an oxidation potential greater than that of the Group IIB element, and subsequently recovering at least a portion of a resulting β-fluoroaliphatic carbonate.

12. The claim 11 process, comprising a solvent.

13. The claim 12 process, further comprising an aprotic solvent.

14. The claim 11, 12 or 13 process, wherein said element is present in an ionic form.

15. The claim 11, 12 or 13 process, wherein said element oxidation state is at least zero.

16. The claim 12 or 13 process, wherein said base is a sterically hindered amine.

17. The claim 11, 12 or 13 process, wherein said element oxidation state is at least +2.

18. The claim 11, 12, or 13 process, wherein said element is associated with a halide.

19. The claim 11, 12 or 13 process, wherein said element is coordinated with a ligand.

20. The claim 11, 12 or 13 process, wherein said element is associated with an inorganic halide compound.

21. The claim 11, 12 or 13 process, further comprising a redox co-catalyst.

22. The claim 11, 12 or 13 process, further comprising substantially anhydrous reaction conditions.

23. The claim 11, 12 or 13 process, further comprising a phase transfer agent.

24. The claim 22 process, further comprising a drying agent.

25. The claim 24 process, wherein the drying agent is a molecular sieve.

26. The claim 23 process, wherein the phase transfer agent is an onium halide.

27. The claim 3 process, wherein the solvent is dimethylsulfoxide, the base is 1,2,2,6,6-pentamethylpiperidine, the β-fluoroalkanol is 2,2,2-trifluoroethanol, the Group IIB element mercury is in the form of mercury(II) diacetate.

28. The claim 3 process, wherein the solvent is dimethylsulfoxide, the base is aqueous caustic, the β-fluoroalkanol is 2,2,2-trifluoroethanol, the Group IIB element mercury is in the form of mercury(II) diacetate.

29. A carbonylation process which comprises contacting 2,2,2-trifluoroethanol, carbon monoxide, 1,2,2,6,6-pentamethylpiperidine, mercury(II) diacetate, and subsequently recovering bis(2,2,2-trifluoroethyl) carbonate.

30. The claim 3 process wherein the β-fluoroalkanol is of the formula

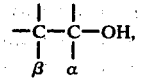

where at least one fluorine atom is associated with at least a β-carbon atom of the β-fluoroalkanol.

31. The claim 30 process wherein the β-fluoroalkanol is a β-trifluoroalkanol containing 2–10 carbon atoms.

32. A carbonylation process which comprises contacting a β-fluoroalkanol selected from

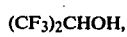

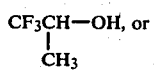

carbon monoxide, a base, and the Group IIB element mercury present in an oxidation state greater than zero, and subsequently recovering at least a portion of a resulting β-fluoroaliphatic carbonate.

33. A carbonylation process which comprises contacting a β-fluoroalkanol, selected from

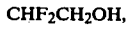

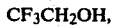

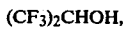

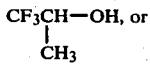

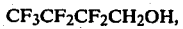

carbon monoxide, a base, the Group IIB element mercury, and an oxidant having an oxidation potential greater than that of the Group IIB element, and subsequently recovering at least a portion of a resulting β-fluoroaliphatic carbonate.

* * * * *